US00PP21449P2

(12) United States Plant Patent
Bédard

(10) Patent No.: US PP21,449 P2
(45) Date of Patent: Nov. 9, 2010

(54) SHRUB ROSE PLANT NAMED 'DARCANARD'

(50) Latin Name: *Rosa hybrida*
Varietal Denomination: DARcanard

(75) Inventor: Christian Bédard, Brea, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/587,965

(22) Filed: Oct. 14, 2009

(51) Int. Cl.
*A01H 5/00* (2006.01)

(52) U.S. Cl. ..... Plt./106

(58) Field of Classification Search ..... Plt./106
See application file for complete search history.

*Primary Examiner*—Annette H Para

(57) ABSTRACT

A new variety of Shrub rose suitable for garden decoration, having flowers of medium pink coloration with a lighter reverse.

1 Drawing Sheet

Classification: The present invention relates to a new *Rosa hybrida* plant.

Variety denomination: The new plant has the varietal denomination 'DARcanard'.

BACKGROUND OF THE INVENTION

This invention relates to a new and distinct variety of Shrub rose. The new variety comes from an open pollination of the seed parent known as 'AC Marie-Victorin' (U.S. Plant Pat. No. 11,650).

SUMMARY OF THE INVENTION

Among the features which distinguish the new variety from other presently available and commercial rose cultivars known to the inventor are the following combinations of characteristics: its cordate shape of the terminal leaflets and bases, its heavily suffused rachis, stipule and petiole on the young leaf, its excellent resistance to powdery mildew, black spot, downy mildew and rust, its high degree of cold hardiness and its many petals and petaloids. The plant has a spreading to somewhat climbing growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'DARcanard' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'AC Marie-Victorin' by the following combination of characteristics: whereas 'DARcanard' bears very double flowers (about 29 to 74 petals) of medium pink coloration with a lighter reverse, 'AC Marie-Victorin' bears double flowers of attractive peach-pink coloration with significantly lower range of petals (about 34 to 42 petals). The new variety is classified as a shrub rose with a spreading to somewhat climbing tall growing habit (about 150 to about 180 cm. in height), whereas the seed parent is classified as a shrub rose with a significantly shorter growing habit (about 100 cm. in height).

The pollen parent of the new variety is unknown.

COMPARISON WITH THE CLOSEST COMMERCIALLY AVAILABLE CULTIVAR

The new variety may be distinguished from its closest commercially available cultivar, John Cabot, by the following combination of characteristics: whereas 'DARcanard' bears very double flowers (about 29 to 74 petals) of medium pink coloration with a lighter reverse, John Cabot bears double flowers of fuchsia tinted red coloration with significantly lower range of petals (about 40 petals).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of September. Phenotypic expression may vary with environmental, cultural and climatic conditions, as well as differences in conditions of light and soil.

FLOWER

The new variety usually bears its flowers in clusters of five to nine or more per stem. Flowers are borne in moderately regular rounded clusters on strong medium to long stems (about 33 to about 80 cm.). Outdoors, the plant blooms abundantly and nearly continuously during the growing season. The flowers have a slight fruity to apple-like fragrance.

BUD

The peduncle is about 1.4 to about 4.2 cm. in length, of average caliper (about 0.15 to about 0.2 cm. in diameter), and usually erect. It is somewhat rough, with many stipitate glands and few hairs. Peduncle color is between 144A and 146C often heavily suffused, especially on the side exposed to the sun, with between 187B and 187A.

Before the calyx breaks, the bud is about 0.7 to about 1.4 cm. in diameter at the widest point, about 0.9 to about 1.6 cm. in length, and globular in shape. The surface of the bud bears few foliaceous appendages and many stipitate glands, usually with slender entire foliaceous parts extending beyond the tip of the bud about ¼ or more of its length. Bud color is between 137C and 146B often heavily suffused, especially on the side exposed to the sun, with between 187A and 187B.

The sepals are about 1.3 to about 2.0 cm. in length and about 0.6 to about 0:9 cm. in width at the widest point. The outer surface color of the sepal is between 137C and 146B often heavily suffused, especially on the side exposed to the sun, with between 187A and 187B. The inner surface color of the sepal is near 138B broadly bordered by near 137A. After the sepals open, the inner surface color is often moderately suffused, especially on the area exposed to the sun, with between 187A and 183A. The inner surface of the sepal is covered with fine wooly tomentum; sepal margins are lined with many stipitate glands and some hairs.

The receptacle of the flower is of somewhat short length (about 0.3 to about 0.4 cm.) and average in caliper (about 0.5 to about 0.7 cm. in diameter). The receptacle is cup-shaped in form. Its surface is smooth with some hairs and few stipitate glands and with thick fleshy walls. The receptacle color is between 146B and 137C often heavily suffused, especially on the side exposed to the sun, with between 187B and 187A.

As the petals open (after the calyx breaks), the bud is about 1.5 to about 2.3 cm. in diameter at the widest point, about 1.9 to about 2.4 cm. in length, and moderately ovoid in form. The color of the under surfaces of the newly opened petals is between 57C and 61C. At the point where the petal attaches, there is a somewhat large zone of between 1D and 2D. The color of the upper surfaces of the newly opened petals is between 57A and 57B. At the point where the petal attaches, there is a moderately large zone of between 2C and 3D.

BLOOM

When fully open, the bloom ranges from about 6.1 to about 9.4 cm. in diameter. Petalage is very double with about 29 to 74 petals and about 58 to 69 petaloids irregularly arranged. When partially open, the bloom form is very cupped to moderately globular, and the petals are loosely spiraled to cupped with petal edges somewhat reflexed outward. When fully open, the bloom form is cupped, and the petals are loosely cupped with petal edges somewhat reflexed outward.

PETALS

The substance of the petals is somewhat slight and of moderately thin thickness, with upper surfaces slightly shiny to somewhat satiny and under surfaces moderately shiny. The petals are about 1.8 to about 4.7 cm. in length and about 0.8 to about 3.7 cm. in width at the widest point. Petal margins are entire.

The outer petals are broadly obovate in shape with rounded apices and sometimes slightly notched with one notch.

The inner petals are moderately oblanceolate in shape with rounded apices.

Petaloids are about 1.1 to about 2.4 cm. in length and about 0.7 to about 2.1 cm. in width at the widest point. Petaloids are irregularly shaped moderately oblanceolate to somewhat obovate with rounded apices.

NEWLY OPENED FLOWER

The under surface color of the outer, intermediate and inner petals is between 66C and 61C. At the point where the petal attaches, there is a somewhat large zone of near 2D. The upper surface color of the outer, intermediate and inner petals is between 57B and 61C. At the point where the petal attaches, there is a moderately large zone of between 3C and 4B.

The under and upper surface colors of the petaloids are similar in coloration to the upper and under surfaces of the intermediate and inner petals.

The general tonality of the newly opened flower is between 57B and 61C.

THREE-DAY-OLD FLOWER

The under surface color of the outer, intermediate and inner petals is between 66C and 67C. At the point where the petal attaches, there is a somewhat large zone of between 155C and 155A. The upper surface color of the outer, intermediate and inner petals is between 66B and 67C. At the point where the petal attaches, there is a moderately large zone of between 155C and 155A.

The under and upper surface colors of the petaloids are similar in coloration to the upper and under surfaces of the intermediate and inner petals.

The general tonality of the three-day-old flower is between 66B and 67C.

On the spent bloom, the petals usually drop off cleanly.

In September in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are few in number (average about 25) and are arranged regularly about the pistils; many are mixed with petaloids. The filaments are of somewhat short length (about 0.4 to about 0.8 cm.) most with anthers. Filaments are between 13C and 14C in color sometimes lightly suffused with near 53B. The anthers are of medium size for the class and all open approximately at the same time. Anther color when immature is near 13B on the external part and near 4D on the internal part. Anther color at maturity is near 163B on the external part and near 200C on the internal part. Pollen is somewhat sparse and near 16B in color.

FEMALE REPRODUCTIVE ORGANS

Pistils vary in number (average about 45). The styles are moderately even, average in length (about 0.5 to about 0.8 cm.), somewhat thin in caliper, and loosely bunched to somewhat columnar. Stigma color is between 3C and 4B. Style color is between 1D and 154D sometimes lightly suffused with near 53B. Ovaries are usually all enclosed in the calyx.

Hips are moderately short in length (about 0.9 to about 1.4 cm.), moderately globular the somewhat rounded in form, and between 30A and 32A in color when ripe. The hip surface is smooth with some hairs and few stipitate glands and with thick fleshy walls. The sepals are moderately fugacious, and usually straight in shape.

The seeds are irregularly rounded, smooth in texture, approximately 6 to about 15 per hip, about 0.3 to about 0.6 cm. in diameter at the widest point and between 162B and 161B in color.

FOLIAGE

The compound leaves are usually comprised of three to seven leaflets and are borne abundantly. The seven-leaflet leaves are about 7.3 to about 15.1 cm. in length and about 5.2 to about 12.7 cm. in width at the widest point, very crisp in texture, and moderately glossy in finish on the upper side and matte in finish in the under side. The terminal leaflets are about 2.8 to about 6.6 cm. in length and about 1.9 to about 5.4 cm. in width at the widest point, shaped moderately cordate to somewhat ovate with acute to somewhat acuminate apices and cordate bases. Their margins are usually simply serrate.

The upper surface color of the mature leaf is between 137A and 147A. The under surface color of the mature leaf is between 146B and 148A. The upper surface color of the young leaf is between 146A and 146B, usually moderately suffused, especially toward the leaf edge and the mid-rib, with between 187B and 187A. The under surface color of the young leaf is between 146C and 146B, usually heavily suffused with between 187B and 187A.

The rachis is somewhat heavy in caliper and rough. The upper side is shallowly grooved with few hairs and stipitate glands on the edges of the grooves. The under side of the rachis is rough with few stipitate glands and some small prickles. The rachis color is near 145A on the under side and near 146B on the upper side often heavily suffused on the young leaf with between 187B and 187A.

The stipules are about 1.0 to about 1.6 cm. in length and moderately wide (about 0.8 to about 1.1 cm.) with somewhat short straight points that usually turn out at an angle of more than 45 degrees. The stipule color is between 138A and 138B often heavily suffused on the young leaf with between 187B and 187A.

The petiole is somewhat heavy in caliper and rough. The upper side is shallowly grooved with few hairs and stipitate glands on the edges of the grooves. The under side of the petiole is rough with few stipitate glands and some small prickles. The petiole is about 0.2 to about 0.6 cm. in length and about 0.1 to about 0.2 cm in diameter at the widest point. The petiole color is near 145A on the under side and near 146B on the upper side often heavily suffused on the young leaf with between 187B and 187A.

The plant displays an excellent resistance to powdery mildew, black spot, downy mildew and rust as compared to other commercial varieties grown under comparable conditions in Pomona, California. The variety is very winter hardy, surviving winter in USDA zone 3 without any winter protection. The plant's drought and heat tolerance are yet to be determined.

GROWTH

The plant has a spreading to somewhat climbing tall growing habit (about 150 to about 180 cm. in height and about 65 to about 80 cm. spread at the widest point), with moderately full branching. It displays very vigorous growth and the canes are of somewhat heavy caliper for the class (about 1.5 to about 2.5 cm. in width at the widest point).

The color of the major stems is between 146C and 152B. They bear some large prickles that are about 0.4 to about 0.6 cm. in length. The large prickles are moderately angled to somewhat hooked downward with a moderately long narrow oval base; prickle color is between 165B and 166B. The major stem bears few small prickles of similar shape and coloration.

The color of the branches is near 146C. They bear some large prickles which are of similar size and shape to the large prickles on the major stems; prickle color is between 165B and 166B. The branches bear few small prickles of similar shape and coloration.

The color of the new shoots is between 146D and 145A often heavily suffused with between 187B and 187A. They bear few large prickles which are of similar size and shape to the large prickles on the major stems; prickle color is between 165B and 166B. The shoots bear few small prickles of similar shape and coloration.

I claim:

1. A new and distinct Shrub rose plant of the variety substantially as described and illustrated herein.

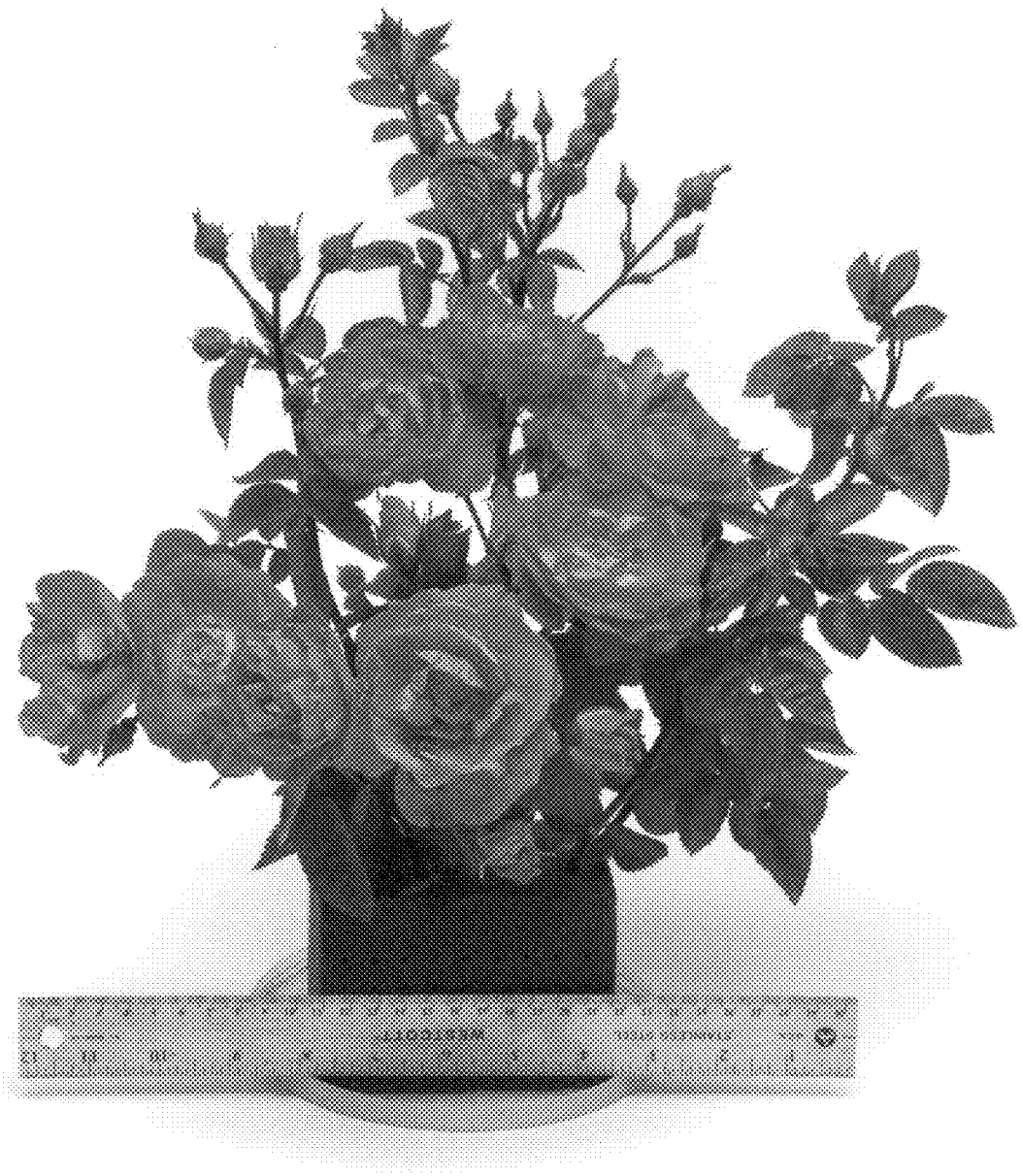

* * * * *